United States Patent [19]
Nakada et al.

[11] Patent Number: 5,618,794
[45] Date of Patent: Apr. 8, 1997

[54] α-GLYCOSYL DERIVATIVE OF CATECHOLAMINE OR ITS SALT, AND ITS PREPARATION AND USES

[75] Inventors: Tetsuya Nakada, Okayama; Michio Kubota, Osaka, both of Japan

[73] Assignee: Kabushiki Kaisha Hayashibara Seibutsu Kagaku Kenkyujo, Okayama, Japan

[21] Appl. No.: 483,260

[22] Filed: Jun. 7, 1995

Related U.S. Application Data

[62] Division of Ser. No. 297,527, Aug. 26, 1994, abandoned, which is a division of Ser. No. 57,915, May 7, 1993, Pat. No. 5,380,837.

[51] Int. Cl.$^6$ .......................... C07H 15/20; A61K 31/70; C12P 19/44
[52] U.S. Cl. .................. 514/25; 514/53; 514/54; 536/17.9; 435/74
[58] Field of Search .................. 536/17.9; 514/25, 514/53, 54; 435/74

[56] References Cited

PUBLICATIONS

Yago et al.; "The identification of fiber N–Acyldopamine Glucosides in the left colleterial gland of the praying mantid, . . .", Insect Biochem., vol. 14, No. 5 (1984) pp. 487–489.

Seikagaku–Jikken Koza, "Metabolism of amino acids, and in vivo amines", The Japanese Biochemical Society, Part B, vol. 11, pp. 725–753 (1977).

"Denpun–Kagaku–Handbook (Handbook of Starch Science)", pp. 190 (1984), published by Asakura Shoten Publisher.

The Journal of Biological Chemistry; vol. 153, Baltimore (1944).

Ishizaki et al.; "Further studies on dopamine and N–acyldopamine during the pupal stage of papilio xuthus (lepidoptera: papiliondae)"; Comp. Biochem. Physiol., vol. 97B, No. 3, pp. 563–567, 1990.

Kebabian et al; "Dopamine–sensitive adenylate cyclase in caudate nuclus of rat brain, and its similarity to the 'Dopamine Receptor'", Proc. Nat. Acad. Sci. USA, vol. 69, No. 8, pp. 2145–2149 (Aug. 1972).

Mueller, D.D. et al.; "$^1$H and $^{13}$C NMR of 3–0 and 4–0 conjugates of dopamine and other catecholamines", Bioconjugate Chem. 4:47–53 (1993).

Primary Examiner—John Kight
Assistant Examiner—Everett White
Attorney, Agent, or Firm—Browdy and Neimark

[57] ABSTRACT

Disclosed is a novel α-glycosyl derivative of a catecholamine or its salt, said α-glycosyl derivative being prepared by allowing a saccharide-transferring enzyme together with or without glucoamylase to act on a solution containing an α-glycosyl saccharide and one of catecholamines in order to form an α-glycosyl derivative of said catecholamines, and recovering the resultant α-glycosyl derivative. The α-glycosyl derivative overcomes conventional drawbacks of catecholamines, and does not substantially exhibit or have a reducing activity and undesirable toxicity, but has a relatively-high stability and exerts the inherent physiological activities of catecholamines in vivo. Thus, the α-glycosyl derivative is advantageously used as a variety of pharmaceuticals in the form of an injection, tablet, etc.

7 Claims, 3 Drawing Sheets

α-GLYCOSYL DERIVATIVE OF CATECHOLAMINE OR ITS SALT, AND ITS PREPARATION AND USES

This is a division of application Ser. No. 08/297,527, filed Aug. 26, 1994, now abandoned, which is a division of application Ser. No. 08/057,915, filed May 7, 1993, now U.S. Pat. No. 5,380,837.

BACKGROUND OF THE INVENTION

1. Field of the Invention

The present invention relates to a novel α-glycosyl derivative of a catecholamine or its salt (the wording "α-glycosyl derivative of a catecholamine or its salt" will be designated as "α-glycosyl catecholamine" hereinafter, if specified otherwise), and to its preparation and uses, more particularly, to an α-glycosyl catecholamine which does not substantially exhibit a reducing activity and turns green on the anthrone-sulfuric acid method, and to a process for preparing an α-glycosyl catecholamine, as well as to its uses, said process comprising allowing a saccharide-transferring enzyme to act on a solution containing an α-glycosyl saccharide and one of catecholamines and their salts (the wording "catecholamines and their salts" will be designated as "catecholamines" hereinafter, if specified otherwise) in order to form an α-glycosyl catecholamine, and recovering the resultant α-glycosyl catecholamine.

2. Description of the Prior Art

As described in publications such as *The New England Journal of Medicine,* Vol. 280, No. 7, pp. 337–345 (1969); *Proceedings of the National Academy of Sciences of the United States of America,* No. 69, No. 8, pp. 2145–2149 (1972); and *Seikagaku-Jikken Koza,* titled "Metabolism of amino acids, and in vivo amines", Part B, Vol. 11, pp. 725–753 (1977), edited by The Japanese Biochemical Society, published by Tokyo-Kagaku-Dozin Co., Ltd., Tokyo, Japan, catecholamines are one of biologically-active amines, and have been known as a compound which exhibits a variety of pharmacological activities, and because of these they have been used as an anti-Parkinson's disease agent or anti-parkinsonism agent, mydriatic, hypotensor, antitussive, expectorant, adrenal medullary hormone, vasohypertonic and cordial, as well as an agent for autonomic nerve.

Although the catecholamines have a reducing activity and a relatively-high stability in an aqueous acid solution, they are readily oxidized under atmospheric conditions to change their colors and to form sediments, and because of these their actual uses are inevitably highly restricted. They also have a drawback, i.e. they have a phenolic hydroxyl group which allows them to be conjugated, methylated and oxidized in a relatively-high level when orally administered and passed through gastrointestinal walls.

As described in *Insect Biochemistry,* Vol. 14, No. 5, pp. 487–489 (1984) and *Comparative Biochemistry and Physiology, Part B, Comparative Biochemistry,* Vol. 97B, No. 3, pp. 563–567 (1990), glycosylated catecholamines are found in natural compounds in a β-glucosylated form, but have not yet been artificially synthesized via an enzymatic technique, and the industrial-scale preparation has been deemed difficult.

It has been a great demand to overcome drawbacks of conventional catecholamines, and to establish a novel catecholamine derivative which exerts a satisfiable physiological activity in vivo without a fear of causing undesirable side-effects.

SUMMARY OF THE INVENTION

The present invention was made to overcome the above conventional drawbacks, more particularly, we studied to obtain a novel catecholamine derivative via a biochemical technique.

As a result, we found that a novel α-glycosyl catecholamine is prepared by allowing a saccharide-transferring enzyme to act on a solution containing an α-glucosyl saccharide and one of catecholamines whereby one or more D-glucose residues attach by an α-linkage of hydroxyl groups of the C-3 and C-4 of the catecholamine moiety, said resultant α-glycosyl catecholamine having a relatively-high stability and substantial no reducing activity, as well as being readily hydrolyzed in vivo, and established the preparation. Thus, we accomplished this invention.

DETAILED DESCRIPTION OF THE INVENTION

The wording "catecholamines" as referred to in the invention mean chemical compounds which have a catechol skeleton having a side chain of ethylamine as shown by the formula 1.

Formula 1:

wherein R1 means a member selected from —H and —OH; R2 and R3, a member selected from —H, —COOH and lower alkyl groups having 1–4 carbon atoms; and R4, a member selected from —H and lower alkyl groups having 1–4 carbon atoms.

The catecholamines advantageously usable in the invention are, for example, dopa wherein R1 in the formula 1 is —H, and R2 and R3 are differently —H or —COOH, i.e. R2 and R3 are not the same; dopamine wherein R1, R2, R3 and R4 are —H; α-methyldopa wherein R1 and R4 are —H, and R2 and R3 are differently —CH₃ or —COOH; threo-DOPS or droxidopa wherein R1 is —OH and R2 and R3 are differently —H or —COOH; adrenaline or einephrine wherein R1 is —OH, R2 and R3 are —H, and R4 is CH₃; noradrenaline or norepinephrine wherein R1 is —OH, R2, R3 and R4 are —H; isoproterenol wherein R1 is —OH, R2 and R3 are —H, and R4 is CH(CH₃)CH₃; and their salts such as hydrochlorides, tartrates and sulfates.

Any α-glucosyl saccharide can be used in the invention as long as it can form an α-glycosyl catecholamine when subjected together with one of catecholamines to the action of a saccharide-transferring enzyme. For example, liquefied starch, gelatinized starch, and partial starch hydrolyzates such as amylose, dextrins, cyclodextrins and maltooligosaccharides can be suitably chosen.

In order to facilitate the formation of the present α-glycosyl catecholamine, an α-glucosyl saccharide suitable for a saccharide-transferring enzyme is chosen. For example, in case of using α-glucosidase (EC 3.2.1.20) as a saccharide-transferring enzyme, maltooligosaccharides such as maltose, maltotriose and maltotetraose, and partial starch hydrolyzates having a dextrose equivalent (DE) of about 10–70 are suitably used. In case of using cyclomaltodextrin glucanotransferase (EC 2.4.1.19), cyclodextrins, gelatinized starches having a DE of one or lower and partial starch hydrolyzates having a DE of about 60 or lower are suitably used. In case of using α-amylase (EC 3.2.1.1), gelatinized starches having a DE of one or lower and partial starch hydrolyzates having a DE of about 30 or lower are suitably used.

The α-glycosyl saccharides usable in the invention are suitably subjected to an enzymatic reaction in an amount of about 0.5–100-fold, preferably, about 2–20-fold higher concentration of that of catecholamines. In such an enzymatic reaction, the solutions containing catecholamines suitably used in the invention are those which contain catecholamines to the possible highest level, for example, those in the form of suspension or solution prepared by dissolving catecholamines in a solvent at a relatively-high temperature or by dissolving the catecholamines in an inorganic solvent to give a concentration of about one w/v % or higher, preferably, about 2–20.0 w/v %.

Any saccharide-transferring enzyme can be used in the invention as long as it can form an α-glycosyl catecholamine without decomposing material catecholamines when allowed to act on solutions containing the material catecholamines and an α-glycosyl saccharide as a suitable substrate for the enzyme.

Examples of such a saccharide-transferring enzyme suitably chosen in the invention are, for example, α-glucosidases derived from enzymes of animal- and plant-tissues such as a pig liver and buckwheat seed, and those derived from cultures prepared by cultivating in a nutrient culture medium fungi such as microorganisms of the genera Mucor and Penicillium, and yeasts such as microorganisms of the genus Saccharomyces; cyclomaltodextrin glucanotransferases derived from microorganisms of the genera Bacillus and Klebsiella; and α-amylases derived from microorganisms of the genus Bacillus and cultures of fungi of the genus Aspergillus.

The saccharide-transferring enzymes should not necessarily be purified prior to their uses as long as they fulfill the above requirements, and usually the crude preparations can attain the present object. If necessary, the crude preparations can be purified by conventional purifications. Commercially available saccharide-transferring enzymes can be also used in the invention.

The amount and reaction time of such an enzyme are closely dependent each other, and usually an adequate amount of enzyme which completes the enzymatic reaction within about 5–80 hours is chosen from an economical viewpoint. Immobilized enzymes can be suitably used repeatedly in a bachwise- or a continuous-manner. In order to prevent the decomposition of material catecholamines in a reaction mixture, the present enzymatic reaction should be carried out under light-shielded and anaerobic conditions as much as possible.

The α-glycosyl catecholamines thus obtained can be purified with a gel filtration agent by using the molecular separation effect to separate the α-glycosyl catecholamines from contaminants such as intact catecholamines and α-glucosyl saccharides.

The separated α-glycosyl catecholamines do not substantially exhibit a reducing activity and turn green on the anthrone-sulfuric acid method as described in *Denpun-Kagaku-Handbook* (*Handbook of Starch Science*), pp. 190 (1984), published by Asakura Shoten publisher, Tokyo, Japan, or in *Methods in Carbohydrate Chemistry*, Vol. 1, pp. 478–479 (1962). While the resultant intact catecholamines have a reducing activity and exhibit no coloration on the anthrone-sulfuric acid method. Because of these, the present α-glycosyl catecholamines and intact catecholamines are readily distinguishable. The α-glycosyl catecholamines have an ultraviolet absorption spectrum around the wavelength of 280 nm, and this also readily distinguishes the α-glycosyl catecholamines from intact catecholamines.

The wording "a gel filtration agent" as referred to in the invention means those which have an adequate range of molecular weight fractionation suitable for an effective separation of α-glycosyl catecholamines from contaminants such as intact catecholamines and α-glucosyl saccharides. For example, commercialized products such as "Toyopearl HW-35" and "Toyopearl HW-40", products of "Toyo Soda Manufacturing Co., Ltd, Tokyo, Japan; "Sephadex® G-10" and Sephadex® G-15", products of Pharmacia LKB Biotechnology, Uppsala, Sweden; and "Bio-Gel P-2", a product of Japan Bio-Rad Laboratories Co., Ltd., Tokyo, Japan.

The α-glycosyl catecholamines can be purified by separating them from contaminants such as intact catecholamines and α-glucosyl saccharides by using an adsorbing agent wherein the adsorbing deferences of substances are utilized.

The adsorbing agents usable in the invention are those which can separate the α-glycosyl catecholamines from contaminants such as intact catecholamines and α-glucosyl saccharides. Examples of such adsorbing agents are cation exchangers, anion exchangers, non-ionic macroporous synthetic resins, and silica adsorbing agents.

After completion of the enzymatic saccharide-transfer reaction, the resultant reaction mixture can be suitably treated with two or more purification methods such as filtration to remove insoluble materials present or formed in the reaction mixture before or after a heat treatment, adsorption to remove proteinaceous substances in the reaction mixture by treating it with magnesium silic acid aluminate or magnesium alminate, and adsorption to remove intact catecholamines in the reaction mixture by treating it with aluminum hydroxide or alumina.

The α-glycosyl catecholamines thus obtained are hydrolyzed by the in vivo enzymes into glucose and catecholamines to exert the inherent activities of catecholamines. The α-glycosyl catecholamines, however, have a phenolic hydroxyl group attached to glucose so that they would be resistant to metabolizations such as conjugation, methylation and oxidation until they are decomposed.

Based on these features, the α-glycosyl catecholamines including their pharmacologically-acceptable acid salts can be advantageously used in an agent with a relatively-high safeness, for example, an anti-Parkinson's disease agent or anti-parkinsonism agent, cordial, mydriatic, hypotensor, antitussive, expectorant, adrenomedullary hormone and vasohypertonic, as well as an agent for autonomic nerve.

The α-glycosyl catecholamines do not substantially exhibit a reducing activity and have a relatively-high stability as compared with intact catecholamines, and from this viewpoint the α-glycosyl catecholamines are more advantageous than intact catecholamines.

The wording "it does not substantially exhibit a reducing activity" as referred to in the invention means that it is not substantially colored on the Nelson-Somogyi's method as described in *Journal of Biological Chemistry*, No. 153, pp. 375–380 (1944).

The α-glycosyl catecholamines including their pharmacologically-acceptable acid salts can be administered to a recipient by conventional oral or parenteral administration methods such as an injection and suppository. They are formed into a pharmaceutical agent in combination with a carrier in the form of liquid or solid which does not affect their activities.

Examples of such a pharmaceutical agent are those in the form of syrup, suspension, injection, powder, granule, capsule, tablet and buccal. The solid carriers usable in the invention which are admixable with the α-glycosyl catecholamines and their pharmacologically-acceptable acid salts are, for example, corn starch, lactose mannitol, pullulan, talc, stearin, magnesium stearate and gums.

The liquid carriers for an injection and suspension usable in the invention are, for example, water, plant oils, emulsifiers and surface active agents.

The pharmacologically-acceptable acid salts of α-glycosyl catechclamines include those which are free of toxicity and preparable by allowing the α-glycosyl catecholamines to react with an appropriate organic or inorganic acid such as hydrochloride, hydrobromide, sulfate, bisulfite, acetate, oxalate, valerianate, oleate, laurate, lactate, succinate and tartrate.

The dose of the α-glycosyl catecholamines according to the present invention is suitably controlled dependently on the content, administration route and administration frequency. Usually, a recommendable dose of the α-glycosyl catecholamines is in the range of about 0.001–10.0 g/day/adult.

The following experiments will explain the present invention in detail.

EXPERIMENT 1

Saccharide-transfer to methyldopa as representative example of catecholamines

EXPERIMENT 1-1

α-Glycosyl methyldopa

EXPERIMENT 1-1-(1)

Enzymatic reaction

To one part by weight of methyldopa and 4 parts by weight of α-cyclodextrin was added 20 parts by weight of water, and the resultant mixture was adjusted to pH 5.5, added with 50 units/g α-cyclodextrin of a cyclomaltodextrin glucanotransferase specimen commercialized by Hayashibara Biochemical Laboratories Inc., Okayama, Japan, allowed to react at 50° C. for 16 hours, and heated to inactivate the remaining enzyme.

EXPERIMENT 1-1-(2)

Separation and detection on thin-layer chromatography

A reaction mixture obtained by the method in Experiment 1-1-(1) was filtered, and the filtrate was diluted 4 times with water. A sample of the resultant solution was spotted on "Kieselgel 60F254", a thin-layer plate commercialized by Merck & Co., Inc., Rahway, N.J., USA, and the plate was dried. A mixture solution consisting of butanol, acetic acid and water (4:1:1 by volume) was used as a developing solvent, and the spotted sample was developed once at an ambient temperature. The ninhydrin coloration was used to detect α-glycosyl methyldopas which had been enzymatically formed by using methyldopa as a substrate: After the development, the thin-layer plate was successively dried, sprayed with a ninhydrin reagent prepared by dissolving 0.2 g ninhydrin in 50 ml n-butanol saturated with 0.1M citrate buffer (pH 5.0), and dried. The resultant plate was heated at 100° C. for 5 minutes to effect coloration of methyldopa and α-glycosyl methyldopas.

The results of the measured mobilities of intact methyldopa and α-glycosyl methyldopas were as shown in Table 1.

TABLE 1

| Sample | Mobility | |
|---|---|---|
| α-Glycosyl methyldodas | 0.21 | Present invention |
|  | 0.18 |  |
|  | 0.12 |  |
|  | 0.10 |  |
|  | 0.07 |  |
|  | 0.04 |  |
| Methyldopa | 0.38 | Control |

As evident from the results in Table 1, α-glycosyl methyldopas having a variety of mobilities different from that of methyldopa were detected on the thin-layer plate, and this revealed that the α-glycosyl methyldopas were formed by an enzymatic reaction.

EXPERIMENT 1-2

Formation of α-glucosyl methyldopa

A reaction mixture obtained by the method in Experiment 1-1 was filtered, and the resultant filtrate was added with 10 units/g α-cyclodextrin of glucoamylase (EC 3.2.1.3) specimen commercialized by Seikagaku Kogyo Co., Ltd., Tokyo, Japan, and reacted at pH 5.0 and 55° C. for 16 hours. The resultant reaction mixture was heated to inactivate the remaining enzyme and filtered, and, similarly as in Experiment 1-1 the resultant filtrate was subjected to separation and determination on thin-layer chromatography.

The results of the measurement of the mobilities of methyldopa and α-glucosyl methyldopas were as shown in Table 2.

TABLE 2

| Sample | Mobility | |
|---|---|---|
| α-Glycosyl methyldodas | 0.21 | Present invention |
|  | 0.18 |  |
| Methyldopa | 0.38 | Control |

As evident from the results in Table 2, it was revealed that the α-glycosyl methyldopas as shown in Table 1 were hydrolyzed by glucoamylase to form two α-glucosyl methyldopas having different mobilities from that of methyldopa.

EXPERIMENT 2

Confirmation of α-glucosyl methyldopa

To one part by weight of methyldopa and 4 parts by weight of α-cyclodextrin was added 20 parts by weight of water, and the resultant mixture was adjusted to pH 5.5, and, similarly as in Experiment 1 subjected to a saccharide-transfer reaction and glucoamylase reaction to obtain a solution containing an α-glucosyl methyldopa where D-glucose attaches by an α-linkage to methyldopa.

The reaction mixture thus obtained was fed to a column packed with "Toyopearl HW-40", a gel filtration agent commercialized by Toyo Soda Manufacturing Co., Ltd., Tokyo, Japan, at a flow rate of SV (space Velocity) 0.2, and eluted with water. As a result, the α-glucosyl methyldopa in the reaction mixture was eluted from the column faster than intact methyldopa, and thus the separation of them was attained.

A fraction containing α-glucosyl methyldopa was recovered, concentrated in vacuo and pulverized into a white preparation of α-glucosyl methyldopa in the yield of about 60% against the material methyldopa, on a dry solid basis (d.s.b.).

The preparation thus obtained was dissolved in water to give a concentration of 5 w/v %, fed to "YMC-Pack ODS-5", a column of reversed-phase column chromatography commercialized by YMC Co., Ltd., Kyoto, Japan, and eluted with 20 mM acetate buffer (pH 5.0).

The α-glucosyl methyldopa preparation was eluted at different positions and separated into two components, i.e. the component firstly eluted from the column was named as α-glucosyl methyldopa [I] and the secondary component was named as α-glucosyl methyldopa [II], which were then recovered, concentrated in vacuo and pulverized to obtain white α-glucosyl methyldopa preparations [I] and [II] in the yield of about 30 w/w % and about 20 w/w % against the material methyldopa, d.s.b., respectively.

EXPERIMENT 3

Physicochemical properties of α-glucosyl methyldopa
(1) Solubility in solvent

The α-glucosyl methyldopa preparations [I] and [II] are readily soluble in water; slightly soluble in methanol and ethanol; and insoluble in ether, benzen and chloroform;

(2) Color reaction

The α-glucosyl methyldopa preparations [I] and [II] turn green on the anthrone-sulfuric acid reaction. The preparations are negative on a reducing reaction by the Nelson-Somogy's method;

(3) Ultraviolet absorption spectrum

In order to compare the α-glucosyl methyldopa preparations [I] and [II] with intact methyldopa, their ultraviolet absorption spectra were measured with 0.1N hydrochloric acid solution. Similarly as in intact methyldopa, the α-glucosyl methyldopa preparations [I] and [II] had the adsorption maxima at around 280 nm;

(4) Infrared absorption spectrum

Figure 1:
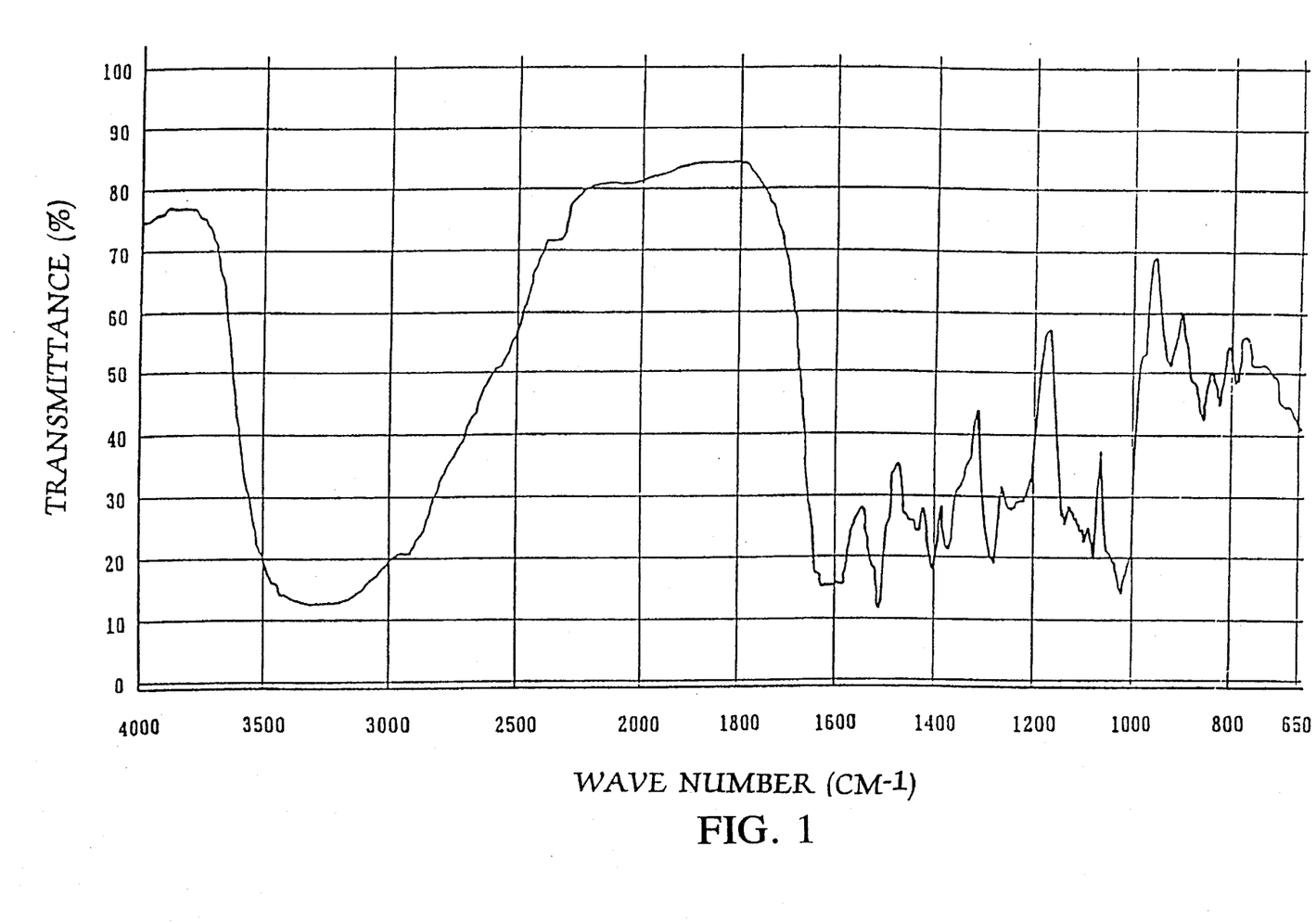
FIG. 1 shows an infrared absorption spectrum of 3-α-glucosyl methyldopa as an example of the present α-glycosyl catecholamines.
Figure 2:
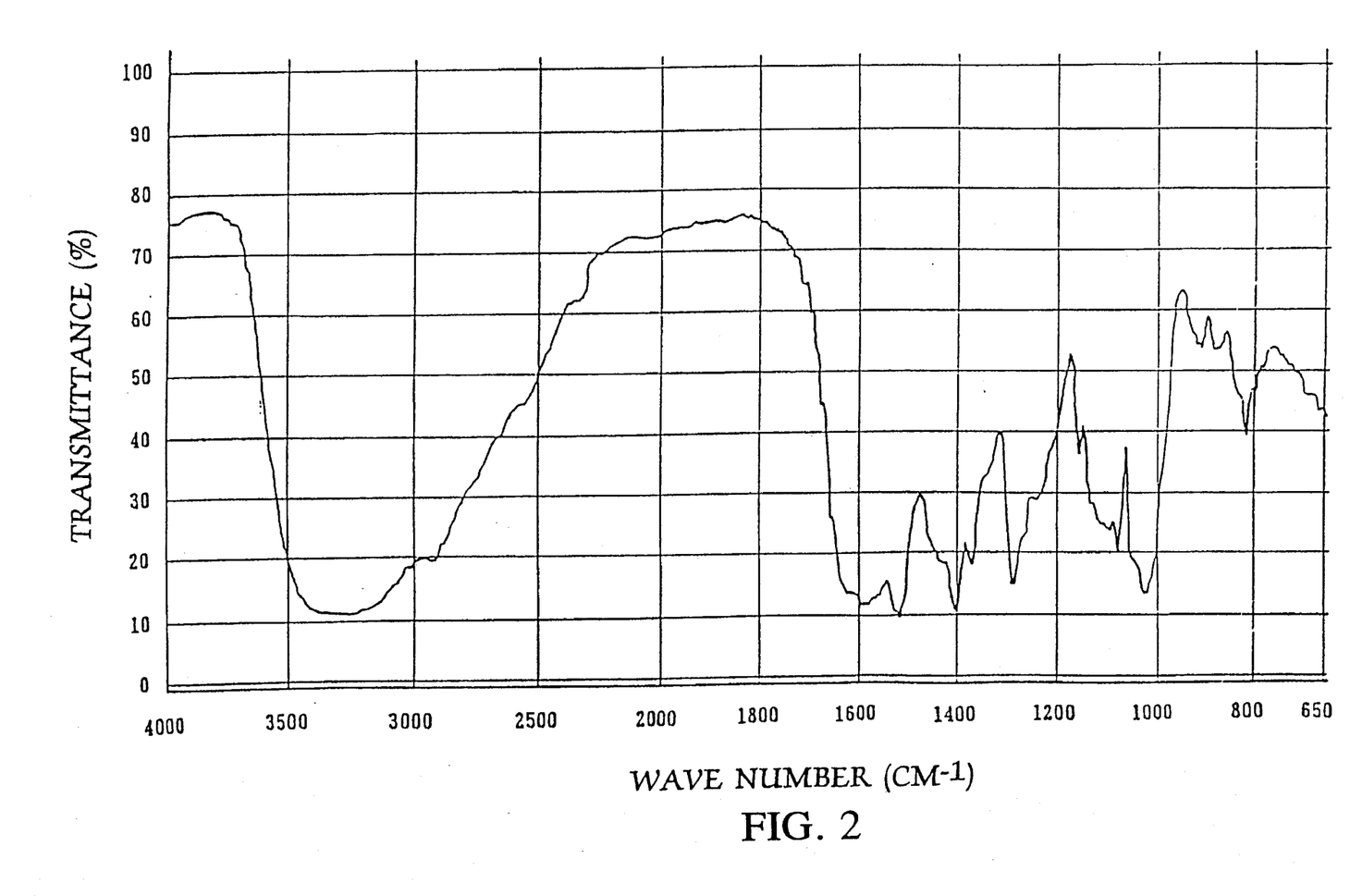
FIG. 2 shows an infrared absorption spectrum of 4-α-glucosyl methyldopa as an example of the present α-glycosyl catecholamines.
Figure 3:
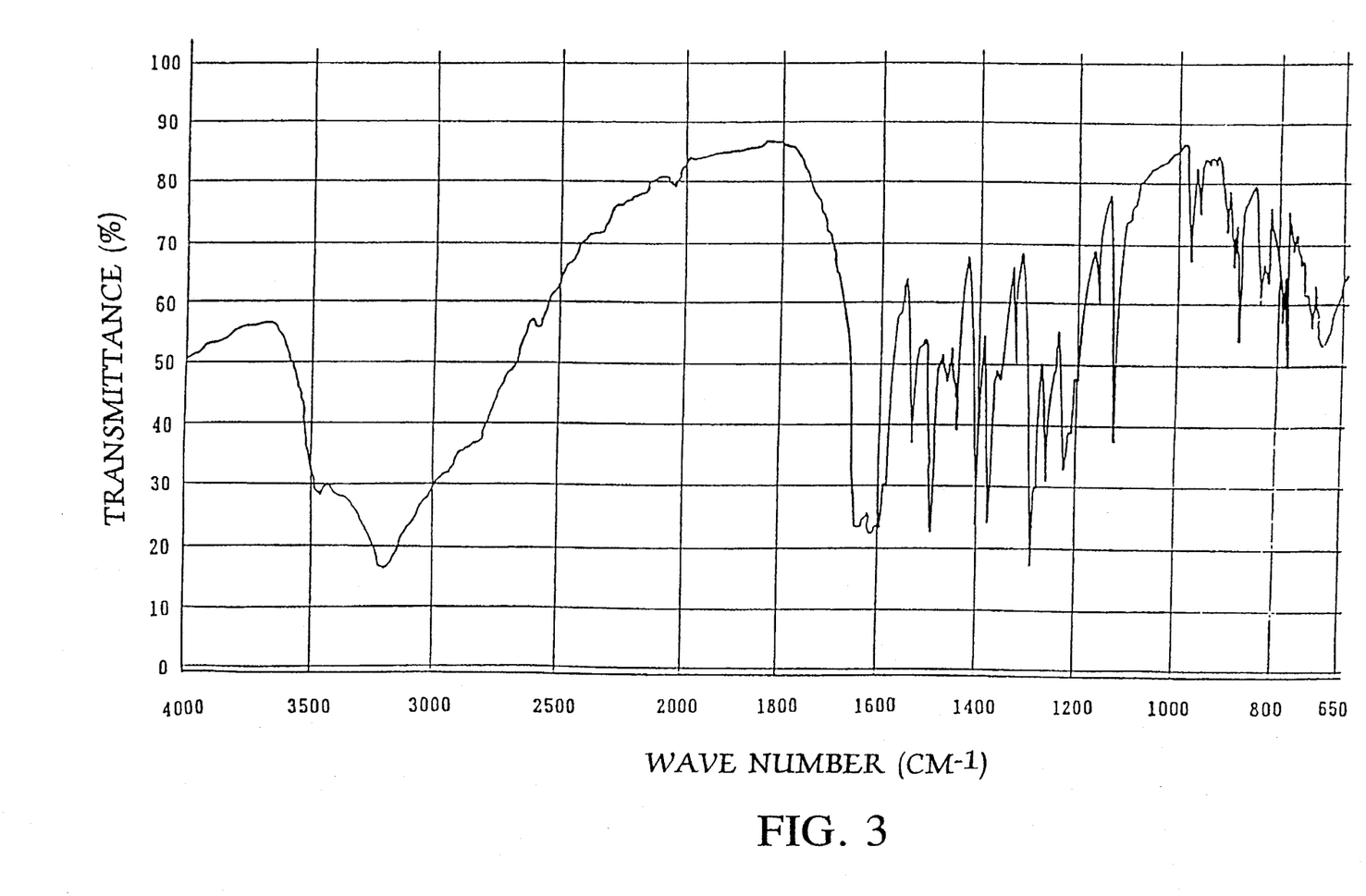
FIG. 3 shows an infrared absorption spectrum of methyldopa as a control.

The infrared absorption spectra of the α-glucosyl methyldopa preparations [I] and [II], wherein D-glucose is attached by α-linkage to methyldopa were measured by the KBr-tablet method. The results were as shown in FIGS. 1 and 2. FIG. 3 shows the infrared absorption spectrum of intact methyldopa as a control;

(5) Silica gel thin-layer chromatogram

α-glucosyl methyldopa preparation [I]:Rf=0.18

α-Glucosyl methyldopa preparation [II]:Rf=0.21

(6) Stability against hydrolysis (a) The α-glucosyl methyldopa preparations [I] and [II] are hydrolyzed by α-glucosidase (EC 3.2.1.20) specimen derived from pig liver to form methyldopa and D-glucose;

(b) The preparations [I] and [II] are not hydrolyzed by β-glucosidase; and (7) NMR spectrum On nuclear magnetic resonance ($^{13}$C-NMR) analysis, the α-glucosyl methyldopa preparations [I] and [II] gave sixteen $^{13}$C signals, and all of which exhibited different chemical shifts. Based on the chemical shifts of 3-O-methyldopa, 4-O-methyldopa and methyl-α-D-glucopyranoside as a standard substance, every carbon atom was assigned to reveal that the α-glucosyl methyldopa preparation [I] is 3-[4-hydroxy-(3-α-D-glucopyranosyl)]-2-methylalanine or has a structure of methyldopa wherein equimolar D-glucose residues attach to the hydroxyl group of the C-3 of methyldopa moiety (hereinafter will be designated as "3-α-D-glucosyl"), and the α-glucosyl methyldopa preparation [II] is 3-[3-hydroxy-(4-α-D-glucopyranosyl)]-2-methylalanine or has a structure of methyldopa wherein equimolar D-glucose residues attach to the hydroxyl group of the C-4 of methyldopa moiety (hereinafter will be designated as "4-α-D-glucosyl").

As described above, the α-glucosyl methyldopas according to the present invention are novel saccharide derivatives of methyldopa having substantially no reducing activity and D-glucose residues attached in α-fashion to either of the hydroxyl groups of the C-3 and C-4 of methyldopa moiety, and readily hydrolyzed in vivo by α-glucosidase to exert the inherent activity of methyldopa.

EXPERIMENT 4

Stability of α-glucosyl methyldopa

Fifty ml aliquots of 100 mM phosphate buffer (pH 8.0) were distributed into 50 ml-flasks, added with the α-glucosyl methyldopa preparation [I] or [II] to give a concentration of 100 ppm, allowed to stand at 25° C., and sampled at a prescribed time interval to determine the stability of the preparation.

Intact methyldopa was used as a control. Five ml solution was collected from each flask at a prescribed time interval, and subjected to the measurement of the coloring degree at 400 nm relating to the oxidation of methyldopa. The results were as shown in Table 3.

TABLE 3

| Sample | Time period (day) | | | | |
|---|---|---|---|---|---|
| | 0 | 1 | 3 | 5 | 9 |
| Methyldopa | 0.01 | 0.75 | 1.22 | 1.11 | 1.04 |
| α-Glucosyl methyldopa preparation [I] | 0.0 | 0.0 | 0.0 | 0.0 | 0.0 |
| α-Glucosyl methyldopa preparation [II] | 0.0 | 0.0 | 0.0 | 0.0 | 0.0 |

The results in Table 3 revealed that the α-glucosyl methyldopa preparations [I] and [II] were much stabler than intact methyldopa.

EXPERIMENT 5

Acute toxicity test

The α-glucosyl methyldopa preparations [I] and [II] were tested for their acute toxicity by orally administering them to 7-week-old dd mice. No mouse died up to the dose of 5 g/kg, and this revealed that the acute toxicities of the preparations were extremely low.

EXPERIMENT 6

Saccharide-transfer to other catecholamines

Four parts by weight of α-cyclodextrin and one part by weight of a catecholamine selected from dopa, dopamine, droxidopa, epinephrine, norepinephrine and isoproterenol were added with 20 parts by weight of water. Similarly as in Experiment 1, the resultant mixture was subjected to a saccharide-transfer reaction and glucoamylase reaction, and each reaction-mixture was subjected to separation and detection on thin-layer chromatography.

FIG. 4 shows the results of the measurement of the mobilities of catecholamines and α-glucosyl catecholamines.

TABLE 4

| Sample | Mobility | |
|---|---|---|
| α-Glucosyl dopa | 0.17 | Present invention |
|  | 0.14 |  |
| α-Glucosyl dopamine | 0.24 | Present invention |
|  | 0.22 |  |
| α-Glucosyl hydroxydopa | 0.15 | Present invention |
|  | 0.13 |  |
| α-Glucosyl epinephrine | 0.19 | Present invention |
|  | 0.17 |  |
| α-Glucosyl norepinephrine | 0.21 | Present invention |
|  | 0.19 |  |
| α-Glucosyl isoproterenol | 0.28 | Present invention |
|  | 0.24 |  |
| Dopa | 0.29 | Control |
| Dopamine | 0.43 | Control |
| Droxidopa | 0.25 | Control |
| Epinephrine | 0.34 | Control |
| Norepinephrine | 0.36 | Control |
| Isoproterenol | 0.47 | Control |

As evident from the results in Table 4, α-glucosyl catecholamines having different mobilities from those of intact catecholamines were detected on a thin-layer plate, and this revealed that the α-glucosyl catecholamines were formed by an enzymatic reaction.

Similarly as in α-glucosyl methyldopa, it was revealed that each α-glucosyl catecholamine formed two types of α-glucosyl catecholamines having different mobilities.

Similarly as in α-glucosyl methyldopa, the α-glucosyl catecholamines were isolated and tested to reveal the following properties:

(i) Turning green on the anthrone-sulfuric acid method;

(ii) Exhibiting substantially no reducing activity on the Melson-Somogyi's method;

(iii) Hydrolyzed by α-glucosidase to form equimolar glucose residues and catecholamines but not hydrolyzed by β-glucosidase; and (iv) Exhibiting a satisfiable stability in an aqueous solution.

Based on the these results, it is speculated that the present α-glycosyl catecholamines have the following formula:

wherein R1 means a member selected from —H and —OH; R2 and R3, a member selected from —H, —COOH and lower alkyl groups having 1–4 carbon atoms; R4, a member selected from —H and lower alkyl groups having 1–4 carbon atoms; and either X or Y is equimolar D-glucose residues attached in α-fashion to a catecholamine moiety and the other is —H.

Accordingly, the α-glycosyl catecholamines according to the present invention are novel saccharide-derivatives of catecholamines wherein D-glucose residues attach in α-fashion to either of hydroxyl groups of the C-3 and C-4 of catecholamine moieties, and readily hydrolyzed by α-glucosidase to exert the inherent physiological activities of catecholamines.

The α-glycosyl catecholamines were tested for their acute toxicities, and the results showed that the toxicities were extremely low similar to that of α-glucosyl methyldopa.

The preferred embodiments according to the present invention will be described in Example A as the present preparation and Example B as the present uses.

EXAMPLE A-1

α-Glucosyl methyldopa

One part by weight of methyldopa and 4 parts by weight of dextrin (DE 10) were added with 20 parts by weight of water, and the mixture was adjusted to pH 5.5, added with 50 units/g dextrin of cyclomaltodextrin glucanotransferase derived from a microorganism of the species *Bacillus stearothermophilus*, and enzymatically reacted at 55° C. for 16 hours. The reaction mixture was heated to inactivate the remaining enzyme and filtered, and the resultant filtrate was added with 5 units/g dextrin of glucoamylase (EC 3.2.1.3) specimen commercialized by Seikagaku Kogyo Co., Ltd., Tokyo, Japan, and enzymatically reacted for 16 hours while keeping the pH and temperature at 5.0 and 55° C.

The reaction mixture thus obtained was heated to inactivate the remaining enzyme and filtered, and the resultant filtrate was fed to a column packed with "Toyopearl HW-40", a gel filtration agent commercialized by Toyo Soda Manufacturing Co., Lid, Tokyo, Japan, at a flow rate of SV 0.2, and eluted with water.

A fraction containing α-glucosyl methyldopa was recovered, concentrated in vacuo and pulverized to obtain a white α-glucosyl methyldopa preparation in the yield of about 55% against the weight of the material methyldopa, d.s.b. High-performance liquid chromatography (HPLC) analysis of the preparation revealed that it contained about 60% 3-α-glucosyl methyldopa and about 40% 4-α-glucosyl methyldopa.

The product can be advantageously used in a pharmaceutical such as a hypotensor in the form of an injection, suspension and tablet with a relatively-high stability.

EXAMPLE A-2

α-Glucosyl methyldopa

To 10 parts by weight of water was added one part by weight of an α-glucosyl methyldopa preparation prepared in accordance with the method in Example A-1, and the mixture was fed to a column packed with "YMC gel ODS-A120", an agent for reverse-phase column chromatography commercialized by YMC Co., Ltd., Kyoto, Japan, fed with 20 mM ammonium acetate buffer (pH 5.0) to effect elution, followed by separately recovering a fraction containing 3-α-glucosyl methyldopa and a fraction containing 4-α-glucosyl methyldopa. Each fraction was concentrated in vacuo and pulverized to obtain a white product of 3-α-glucosyl methyldopa in the yield of about 30% and a white product of 4-α-glucosyl methyldopa in the yield of about 20% against the weight of the material methyldopa, d.s.b.

The α-glucosyl methyldopas can be advantageously used in a pharmaceutical such as a hypotensor in the form of an injection, suspension, granule and tablet with a relatively-high stability.

EXAMPLE A-3

α-Glucosyl methyldopa

EXAMPLE A-3-(1)

Preparation of α-glucosidase specimen

Five hundred parts by weight of a liquid culture medium consisting of water, 4 w/v % maltose, 0.1 w/v % potassium dihydrogenphosphate, 0.1 w/v % ammonium nitrate, 0.05 w/v % magnesium sulfate, 0.05 w/v % potassium chloride, 0.2 w/v % polypeptone, and one w/v % calcium carbonate which was preliminarily subjected to dry sterilization and aseptically added to the culture medium at the seeding time, was inoculated with a seed culture of Mucor javanicus IFO 4570, and incubated at 30° C. for 44 hours under shaking conditions. After completion of the culture, the wet mycelia were recovered, and 48 parts by weight of which was added with 500 parts by weight of 4M urea dissolved in 0.5M acetic acid buffer (pH 5.3). The resultant mixture was allowed to stand at 30° C. for 40 hours and centrifuged.

The resultant supernatant was dialyzed overnight against a flowing water, added with ammonium sulfate to give a saturation degree of 0.9, and allowed to stand at 4° C. overnight. The resultant precipitate was recovered by filtration, dissolved by suspending in 50 parts by weight of 0.01M acetate buffer (pH 5.3), and centrifuged to recover a supernatant as an α-glucosidase specimen.

EXAMPLE A-3-(2)

Preparation of α-glucosyl methyldopa

One part by weight of methyldopa and 10 parts by weight of dextrin (DE 30) were added with 40 parts by weight of water, and the mixture was adjusted to pH 5.5, added with 5 parts by weight an α-glucosidase specimen prepared by the method in Example A-3-(1), and enzymatically reacted at 50° C. for 40 hours. HPLC analysis of the reaction mixture revealed that about 15% of the methyldopa, d.s.b., was converted into a mixture of 3- and 4-α-glucosyl methyldopas. Similarly as in Example A-1, the reaction mixture was purified, concentrated and pulverized to obtain a mixture of 3- and 4-α-glucosyl methyldopas in the yield of about 20%, d.s.b.

Similarly as the product in Example A-1, the product can be advantageously used in a pharmaceutical such as a hypotensor in the form of an injection, suspension, granule and tablet with a relatively-high stability.

EXAMPLE A-4

α-Glucosyl dopamine

One part by weight of dopamine hydrochloride and 4 parts by weight of dextrin (DE 10) were added with 20 parts by weight of water, and the resultant mixture was adjusted to pH 5.5, added with 50 units/g dextrin of cyclomaltodextrin glucanotransferase derived from a microorganism of the species *Bacillus stearothermophilus*, and enzymatically reacted at 55° C. for 16 hours. After completion of the enzymatic reaction, the reaction mixture was heated to inactivate the remaining enzyme, filtered, added with 5 units/g dextrin of glucoamylase (EC 3.2.1.3) specimen commercialized by Seikagaku Kogyo, Co., Ltd., Tokyo, Japan, and enzymatically reacted at pH 5.0 and 55° C. for 16 hours.

Thereafter, the reaction mixture was heated to inactivate the remaining enzyme and filtered, and fed at a flow rate of SV 0.2 to a column packed with "Toyopearl HW-40", a gel filtration agent commercialized by Toyo Soda Manufacturing Co., Ltd., Tokyo, Japan, and the column was fed with water to effect elution. A fraction containing α-glucosyl dopamine was recovered, concentrated in vacuo, and pulverized to obtain a white product of α-glucosyl dopamine in the yield of about 60% against the weight of the material dopamine hydrochloride, d.s.b.

Silica gel thin-layer chromatography and HPLC analyses of the product revealed that the material dopamine hydrochloride was converted into two types of α-glucosyl dopamines similarly as in α-glucosyl methyldopa.

The product can be advantageously used in a pharmaceutical such as a cordial in the form of an injection, suspension, granule and tablet With a relatively-high stability.

EXAMPLE A-5

α-Glucosyl droxidopa

One part by weight of droxidopa and 4 parts by weight of dextrin (DE 10) were added with 20 parts by weight of water, and, similarly as in Example A-1 the resultant mixture was subjected to a saccharide-transfer reaction and glucoamylase reaction, purified by gel chromatography, concentrated and pulverized to obtain a white product of α-glucosyl droxidopa in the yield of about 45% against the weight of the material droxidopa d.s.b.

Silica gel thin-layer chromatography and HPLC analyses of the product revealed that the material droxidopa was converted into two types of α-glucosyl droxidopa similarly as in α-glucosyl methyldopa.

The product can be advantageously used in a pharmaceutical such as an anti-Parkinson's disease agent or antiparkinsonism agent in the form of an injection, suspension, granule and tablet with a relatively-high stability.

EXAMPLE A-6

α-Glucosyl isoproterenol

One part by weight of isoproterenol hydrochloride and 4 parts by weight of dextrin (DE 10) were added with 20 parts by weight of water, and, similarly as in Example A-1 the resultant mixture was subjected to a saccharide-transfer reaction and glucoamylase reaction, purified by gel chromatography, concentrated and pulverized to obtain a white product of α-glucosyl isoproterenol in the yield of about 35% against the weight of the material isoproterenol, d.s.b.

Silica gel thin-layer chromatography and HPLC analyses of the product revealed that the material isoproterenol hydrochloride was converted into two types of α-glucosyl isoproterenols similarly as in α-glucosyl methyldopa.

The product can be advantageously used in a pharmaceutical such as an antitussive and expectorant in the form of an injection, suspension, granule and tablet with a relatively-high stability.

EXAMPLE A-7

α-Glucosyl adrenaline

One part by weight of adrenaline hydrochloride and 4 parts by weight of dextrin (DE 10) were added with 20 parts by weight of water, and, similarly as in Example A-1 the resultant mixture was subjected to a saccharide-transfer reaction and glucoamylase reaction to obtain a solution containing α-glucosyl adrenaline.

The solution was fed at a flow rate of SV 0.2 to a column packed with "Wakogel C-200", a silica adsorbing agent commercialized by Wako Pure Chemical industries Ltd., Tokyo, Japan, in order to adsorb thereon α-glucosyl adrenaline and intact adrenaline. The column was first fed with a mixture solution consisting of butanol and acetic acid (1:1 by volume) to elute intact adrenaline, then fed with a mixture solution of methanol and acetic acid (1:1 by volume) to elute α-glucosyl adrenaline.

A fraction containing α-glucosyl adrenaline was concentrated in vacuo and pulverized to obtain a white product of α-glucosyl adrenaline in the yield of about 35% against the weight of the material adrenaline, d.s.b.

Silica gel thin-layer chromatography and HPLC analyses of the product revealed that the material adrenaline was converted into two types of α-glucosyl adrenalines similarly as in α-glucosyl methyldopa.

The product can be advantageously used in a pharmaceutical such as a mydriatic, vasohypertonic and adrenal medullary hormone in the form of an injection, suspension, granule and tablet with a relatively-high stability.

EXAMPLE B-1

Orally administrable solution

Ten parts by weight of a powdery α-glucosyl dopamine prepared by the method in Example A-4 was mixed to homogeneity with 400 parts by weight of a simple syrup, 400 parts by weight of glycol, 2 parts by weight of ethyl para-hydroxybenzoate, and one part by weight of an orange essence, and the resultant mixture was in usual manner prepared into an orally administrable solution.

EXAMPLE B-2

Injection

A powdery 3-α-glucosyl methyldopa prepared by the method in Example A-2 was dissolved in water, and the resultant solution was in usual manner membrane filtered into a pyrogen-free solution which was then distributed in a 20-ml ampul to give a content of 100 mg 3-α-glucosyl methyldopa, lyophilized, and sealed to obtain the captioned product.

The product alone or in combination with vitamins and minerals can be intramusculary or intravenously administered to a recipient. The product does not necessarily require a light-shielded condition and cold-storage, and has a satisfiable solubility in a solvent such as physiological saline when used.

EXAMPLE B-3

Collyrium

A collyrium was prepared by dissolving in 100 parts by weight of water 1.25 parts by weight of a powdery α-glucosyl adrenaline prepared by the method in Example A-7, 2 parts by weight of boric acid, and 0.2 parts by weight of benzalkonium chloride, subjecting the resultant solution to membrane filtration, and injecting the resultant filtrate into a 10-ml vessel.

The product does not substantially change the color, form sediment, and require a light-shielded condition and cold-storage, and the stability is relatively high.

EXAMPLE B-4

Granule

To 10 parts by weight of a powdery α-glucosyl droxidopa prepared by the method in Example A-5 was mixed to homogeneity, 8 parts by weight of lactose, 5 parts by weight of corn starch and 5 parts by weight of crystalline cellulose, and the resultant mixture was admixed with one part by weight of hydroxy propyl cellulose and 9 parts by weight of ethanol. The resultant mixture was granulated by an extruding granulation and dried with a dryer at 50° C.

The granules thus obtained were sieved to obtain the captioned product having a particle size of 297–1460 μm. The product was injected in a bag to give a content of 500 mg.

EXAMPLE B-5

Tablet

To 30 parts by weight of a powdery 4-α-glucosyl methyldopa prepared by the method in Example A-2 was mixed to homogeneity 300 parts by weight of corn starch, 5 parts by weight of stearic acid, and 5 parts by weight of hydroxy propyl cellulose, and the resultant mixture was in usual manner prepared into a tablet containing 100 mg 4-α-glucosyl methyldopa.

As described above, the present invention has the following features: (i) α-Glycosyl catecholamines, wherein equimolar D-glucose residues attach to either hydroxyl groups of the C-3 and C-4 of catecholamine moieties of catecholamines, are readily prepared via a biochemical technique using a saccharide-transferring enzyme; (ii) the α-glycosyl catecholamines do not substantially exhibit a reducing activity, and this overcomes the drawbacks of catecholamines, i.e. the susceptibility to oxidation; and (iii) the α-glycosyl catecholamines are readily hydrolyzed in vivo into catecholamines and D-glucose to exert the inherent activities of catecholamines.

Accordingly, the α-glycosyl catecholamines according to the present invention can be advantageously used as an agent having a relatively-high stability and safeness, for example, an anti-Parkinson's disease agent or anti-parkinsonism agent, mydriatic, hypotensor, antitussive, expectorant, adrenal medullary hormone, veasohypertonic and cordial, as well as an agent for autonomic nerve.

The establishment of the preparation and uses of the present α-glycosyl catecholamines has a great industrial significance in the pharmaceutical industries and their related chemical-industries.

While there has been described what is at present considered to be the preferred embodiments of the invention, it will be understood the various modifications may be made therein, and it is intended to cover in the appended claims all such modifications as falling within the true spirits and scope of the invention.

We claim:

1. An α-glycosyl derivative of a catecholamine or its salt, which does not substantially exhibit a reducing activity and turns green on the anthrone-sulfuric acid method, said catecholamine being dopa.

2. The α-glycosyl derivative of claim 1, wherein one or more D-glucose residues attach by an α-linkage to either of hydroxyl groups of the C-3 and C-4 of catecholamine moiety of said catecholamine or its salt.

3. The α-glycosyl derivative of claim 2, which is an α-glucosyl derivative of said catecholamine or its salt.

4. A pharmaceutical composition which comprises as an effective ingredient an effective amount of an α-glycosyl derivative of a catecholamine or its salt and a pharmaceutically-acceptable carrier, said catecholamine being dopa.

5. The pharmaceutical composition of claim 4, wherein one or more D-glucose residues attach by an α-linkage to either of hydroxyl groups of the C-3 and C-4 of catecholamine moiety of said catecholamine or its salt.

6. The pharmaceutical composition of claim 4, which is an α-glucosyl derivative of said catecholamine or its salt.

7. The pharmaceutical composition of claim 4, which is in the form of a syrup, suspension, injection, powder, granule, capsule, tablet or buccal.

* * * * *